(12) United States Patent
Fisher et al.

(10) Patent No.: US 9,638,667 B2
(45) Date of Patent: May 2, 2017

(54) DETECTION OF COATING DEFECTS ON BURIED PIPELINES USING MAGNETIC FIELD VARIATIONS WITHIN THE PIPELINE

(71) Applicant: Southwest Research Institute, San Antonio, TX (US)

(72) Inventors: Jay L. Fisher, Alamo Heights, TX (US); Pavan K. Shukla, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 51 days.

(21) Appl. No.: 14/702,346

(22) Filed: May 1, 2015

(65) Prior Publication Data

US 2016/0320343 A1 Nov. 3, 2016

(51) Int. Cl.
*G01N 27/82* (2006.01)

(52) U.S. Cl.
CPC .................................... *G01N 27/82* (2013.01)

(58) Field of Classification Search
USPC .......................................... 324/219–221, 700
See application file for complete search history.

(56) References Cited

U.S. PATENT DOCUMENTS

| | | | | |
|---|---|---|---|---|
| 3,692,650 A | * | 9/1972 | Davis et al. ............ | C23F 13/04 204/196.05 |
| 6,995,677 B2 | | 2/2006 | Aronstam et al. | |
| 2008/0215257 A1 | * | 9/2008 | Stripf ..................... | G01N 29/07 702/38 |
| 2009/0153154 A1 | * | 6/2009 | Hernandez ......... | G01N 33/2852 324/698 |
| 2012/0038376 A1 | * | 2/2012 | Shukla .................... | G01N 17/02 324/700 |
| 2015/0061659 A1 | * | 3/2015 | Freear .................... | G01N 27/82 324/238 |

* cited by examiner

*Primary Examiner* — Vincent Q Nguyen
(74) *Attorney, Agent, or Firm* — Livingston Law Firm

(57) ABSTRACT

A method for in-situ detection of coating defects on a buried pipeline. The pipeline is under cathodic protection or otherwise carries a current applied to its pipe walls. A magnetic field sensor array is placed within the pipeline and moved along its length. As the sensor array travels, it detects the magnetic fields within the pipeline. The sensor output is compared with "expected" data, which represents interior magnetic fields of the pipeline without coating defects. Because electrical current leaks through a coating defect, the current is altered on the pipe wall at the defect. This in turn alters the interior magnetic fields, and a change in the interior magnetic fields indicates a coating defect.

18 Claims, 3 Drawing Sheets

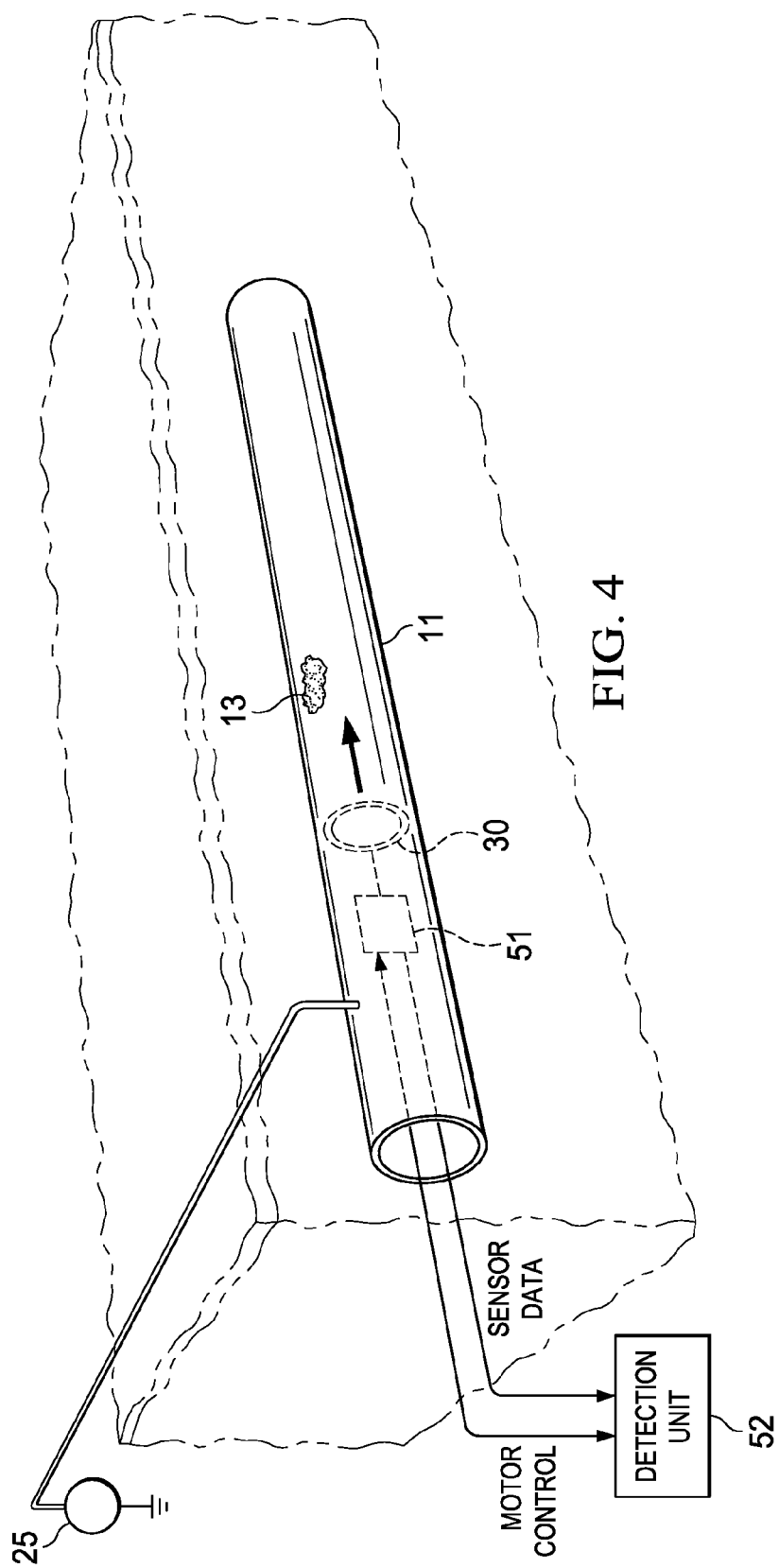

DETECTION OF COATING DEFECTS ON BURIED PIPELINES USING MAGNETIC FIELD VARIATIONS WITHIN THE PIPELINE

TECHNICAL FIELD OF THE INVENTION

This invention relates to detection of coating defects on buried pipelines, and more particularly to detection of magnetic field variations within the pipeline for such purposes.

BACKGROUND OF THE INVENTION

Preventing and detecting pipeline corrosion is a major concern in the pipeline industry. Two approaches to mitigating corrosion are applying pipeline coatings and subjecting pipelines to cathodic protection.

With regard to pipeline coatings, various factory-applied and field-applied coatings are available to cover the outer surface of the metallic pipeline wall. Examples of factory-coating materials are fusion-bonded epoxies, and high-density polyethylene and urethanes. Examples of field-applied coatings are spray coatings such as epoxy, urethane and zinc, various waxes and petrolatum, bitumen-based coatings. Various tapes or other coverings of these or other materials may also be applied to the pipeline.

Cathodic protection may be passive or active. Passive cathodic protection is achieved by electrically connecting the pipeline to another more easily corroded metal to act as the anode of a simulated electrochemical cell. Active cathodic protection uses impressed currents; a current is applied to the conductive pipe wall to force it to act as a cathode.

However, even the best of today's corrosion avoidance techniques do not prevent corrosion at some point. Coatings can degrade, creating areas where the coating material is partially or wholly disbonded from the pipe, limiting protection from corrosion. Also, pipeline installation, especially installation with horizontal direction drilling, can result in extensive coating damage.

Buried pipelines are not easily accessible for corrosion detection. Thus, special techniques have been developed for detecting coating defects and other corrosion without need to expose the pipe surface.

For pipelines that are installed using conventional trench installation, various technologies have been developed for detecting corrosion from the surface above the pipeline. However, pipelines installed using horizontal directional drilling are often installed in this manner to run under features, such as rivers or structures, where trenching is not practical. Thus, there is limited access to the surface above the pipeline. Therefore, pipelines installed using horizontal drilling may require special methods and devices for defect detection.

BRIEF DESCRIPTION OF THE DRAWINGS

FIG. 4 illustrates a system for detecting coating defects, using a magnetic field sensor array.

DETAILED DESCRIPTION OF THE INVENTION

Figure 1:
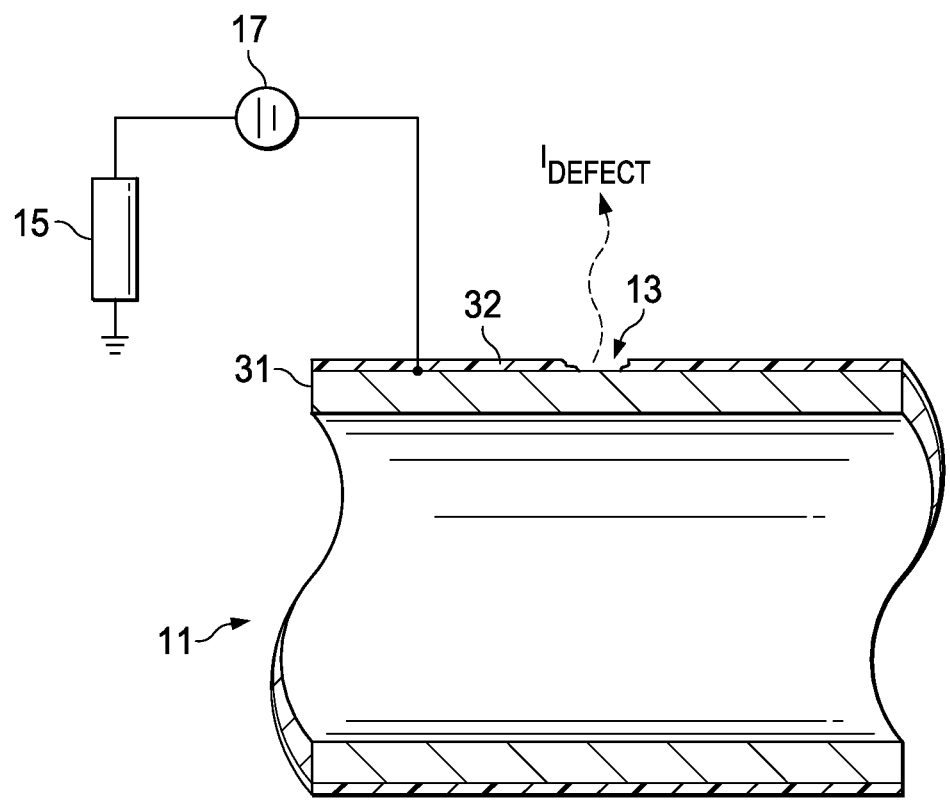
FIG. 1 illustrates a pipeline under cathodic protection and the effect of a coating defect.

As stated in the Background, buried pipelines present access problems for corrosion detection. Of particular concern are pipelines that are installed using horizontal direction drilling. Horizontal direction drilling installation tends to be more likely to damage the coating on the pipeline. Additionally, pipelines installed using horizontal direction drilling are less amenable to corrosion detection techniques designed for trenched pipelines.

For purposes of this description, it is assumed that the pipeline is under cathodic protection or otherwise has an impressed current from a power source. It is also assumed that the pipeline has a protective coating that insulates the pipeline from corrosive moisture in the surrounding environment. As referred to herein, a pipeline "coating" may be any paint or other covering material designed to insulate the structure against corrosion.

The pipeline is further assumed to be "buried", which as used herein, means in soil, underwater, or surrounded by some other electrically conductive environment. The term "soil" is used in a most general sense to mean any surrounding material, typically earth having some degree of moisture. As explained below, in soil or water, if a pipeline has an impressed current, a coating defect will result in current leakage from the pipeline.

The following description is directed to in-situ detection of coating defects on a buried pipeline, whether caused by installation accident or corrosion. The corrosion detection method and system can be used with any pipeline, whether newly installed or existing. As explained below, a magnetic field sensing device is placed inside the pipeline, and an access point for entry into the interior of the pipeline is required. Thus, the method may be performed at any segment on the pipeline where there is access to the interior of the pipeline for placement of the sensing device within the pipeline.

As indicated above, the corrosion detection method described herein is especially useful for pipelines being installed using horizontal direction drilling. A risk of trenchless installation is damage to the pipe coating, which can result in premature external corrosion of metallic pipeline segments because of exposure to soil and water. Coatings can be damaged during pull-through as a result of the forces involved, and by contact with soils, rocks, and other debris present in the borehole. After installation of a pipeline using horizontal directional drilling, it is useful to determine the initial condition of the coating on the pipeline segment immediately after installation. An understanding of the extent of any coating damage will help with making a decision on whether coating damage is too severe to be protected by a cathodic protection system (and thus requiring repair or replacement of the damaged segment before placing it in service), or whether a cathodic protection system can be designed to protect the pipeline segment. The two choices are intertwined; the key input needed for both is the existence and extent of any coating damage.

Pipeline Electrical Current and Coating Defects

FIG. 1 illustrates a buried pipeline 11 with active cathodic protection. The pipeline has a coating 32 on the outer surface of its pipe wall 31. The pipeline 11 is shown as having a defect 13 in its coating 32. The pipe wall 31 is assumed to be electrically conductive, and its coating 32 inhibits or insulates current in the pipe wall 31 from passing to the external environment of the pipeline.

The active cathodic protection is being used to control the corrosion of the pipeline by causing the pipeline to act as a cathode of an electrochemical cell. The pipeline 11 is connected to current source 17, which is also connected to a more easily corroded "sacrificial" metal, which acts as the anode 15. The sacrificial anode 15 then corrodes instead of the protected metal of the pipeline.

When a pipeline is subjected to cathodic protection, a current-potential distribution develops in a moist environment, such as soil or water, near the pipeline. This current-potential distribution is a result of charge flow between the anode 15 and the pipeline 11.

The magnitude and distribution of the charge flow is considerably different near defect sites than at properly coated surfaces of the pipe. This affects current and potential distribution in the soil near the defect sites. An area on the surface of a pipeline having a coating defect, such as defect 13, will generate an electrical current and potential distribution in the neighboring environment. As indicated in FIG. 1, current (represented as $I_{Defect}$), will "leak" and flow from the pipeline into the surrounding environment.

Magnetic Field Detection within Pipeline

Figure 2:
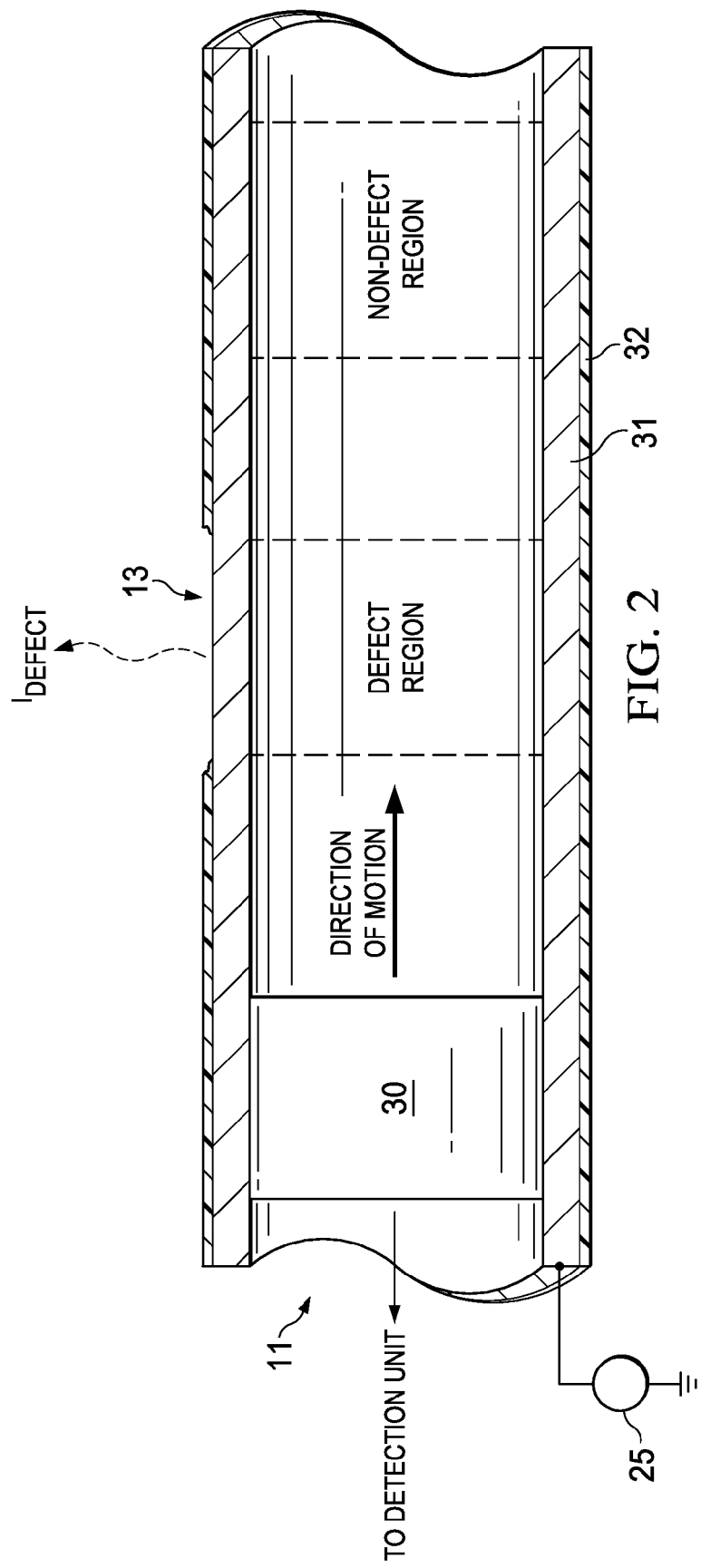
FIG. 2 illustrates a magnetic field sensor array that moves through the pipeline and detects changes in the magnetic field due to a coating defect.

FIG. 2 illustrates a magnetic field sensor array 30 placed within a pipeline 11, in accordance with the invention. The pipeline 11 has an exposed area on the exterior of its pipe wall 31, which is the result of a defect 13 in the pipeline coating 32.

A current flows along the electrically conductive pipe wall 31. This current may be the result of cathodic protection as described above. However, if a cathodic protection system is not in place, a power supply 25 may be electrically connected to pipeline 11 and used to provide current along the pipe wall 31. As explained above, when a current is applied to pipeline 11, a defect such as defect 13, will cause current to flow from the pipeline to a surrounding conductive environment, such as soil or water.

Magnetic field sensor array 30 detects changes in the current flowing along the pipe wall 31 by detecting changes in the magnetic field within the inner wall of the pipeline. Sensor array 30 is pushed or pulled along the length of the pipeline, with the arrow in FIG. 2 indicating a direction of travel.

Figure 3:
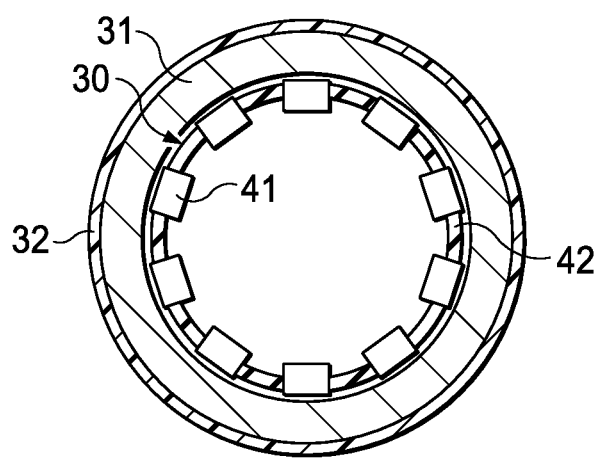
FIG. 3 illustrates one embodiment of the magnetic field sensor array of FIG. 2.

FIG. 3 is a cross-sectional view of pipeline 11, and illustrates an example of sensor array 30 in further detail. Sensor 30 comprises a ring of magnetic field sensors 41. A rigid supporting structure 42 may be used to support and arrange the sensors 41 in the ring shape. An example of a suitable supporting structure is a non-conductive loop to which the sensors 41 are attached. As explained below, a pipeline tool such as a "pig" or other carrier may be used to hold and carry the sensors 41.

Examples of suitable magnetic field sensors 41 are Hall effect sensors, GMR (giant magnetoresistive) sensors, or flux gate magnetometer sensors. There are many approaches for magnetic sensing, and many types of magnetometers. Various MEMS-based magnetic field sensors may also be suitable. Advantages of MEMS-based sensors are that they are small in size, and can be placed close to the measurement location and thereby achieve high spatial resolution.

The outer circumference of the sensor array 30 generally matches, but is smaller than, the inner circumference of the pipe wall. Typically, the pipeline has an inner profile that is round, thus the sensor array is ring-shaped, but other profiles are possible.

The size of the circumference of sensor array 30 relative to the size of the inner circumference of the pipeline is a design feature. In general, the sensitivity of the sensors 41 may determine the desired proximity of the sensors 41 to the inner surface of the pipe wall 31. However, direct contact between the pipe wall 31 and the sensors 41 is not required.

The number of sensors 41 may also vary. At least two sensors 41 will detect localized circumferential variations in the magnetic field, but additional sensors 41 will enhance both sensitivity and localized detection.

Referring again to FIG. 2, as the sensor array 30 travels along the axial length of the pipeline 11, sensors 41 measure the magnetizing forces within the interior of the pipeline. In areas where the coating is damaged and currents leak from the pipe wall to the soil, the currents in the pipe wall decrease, and hence the magnetic field changes. This change is detected by sensors 41. In other words, a circumferential "slice" or "region" of the pipeline near a defect, as sensed by array 30, will have a different magnetic field than a non defective region.

For example, a "perfect" pipe wall with an insulating coating and no coating defects may carry an axial current that is symmetric around the inner circumference of the pipeline. In this case, the measured magnetic field within the pipeline could be uniform or zero. However, if this axial current symmetry is broken by a coating defect, a change in the interior magnetic field can be detected.

Localized circumferential and/or axial magnetic fields will be generated that can be detected by individual sensors 41 located near the defect. These internal magnetic fields can be compared to "expected" magnetic fields, which represent a pipeline with no coating defects. A variation between the sensed and the expected magnetic fields will indicate a coating defect. The comparison can range from a simple visual review of the output from sensor array 30, or a more sophisticated processor-based analysis.

As indicated in FIG. 2 and explained below, the output of the sensors 41 is delivered to a detection unit. Each sensor 41 delivers an output signal to the detection unit so that localized variations in the magnetic field can be detected. The output of sensor 30 can be compared to the expected magnetic fields of the pipeline without defects.

Magnetic Field Detection System

FIG. 4 illustrates a coating defect detection system 500, comprising a sensor array 30 mounted on a carrier 51 and in communication with a detection unit 52. The communication link may be real-time and wired or wireless. However, as explained below, in some embodiments, carrier 51 may have on-board data storage for subsequent reporting to detection unit 52.

Sensor array 30 is inserted into a pipeline 11, and is pushed or pulled along the axial length of the pipeline by carrier 51. Sensor array 30 senses the magnetic fields within pipeline 11 as it travels, and each sensor of the array 30 delivers an output signal to detection unit 52. A set of data from the sensors of array 30 represents the magnetic fields of a "slice" around the inner circumference of the pipeline.

Pipeline 11 has a power source 25 providing current to the pipe wall. The power source 25 may be part of a cathodic protection system or may be otherwise provided. In any event, the power source 25 applies a current to the pipe walls. Ideally, power source 25 is accessible and adjustable, as part of the detection system 500. As explained below, it may be desirable to increase the applied current, making system 500 more sensitive to the pipeline's interior magnetic fields. It may be also desirable to apply an alternating current to the pipeline and detect signals at only that frequency, again to enhance sensitivity.

Pipeline 11 has a coating defect 13, which disrupts the current in the pipe wall and causes changes in the magnetic field inside the pipeline near the defect.

Carrier 51 is representative of various locomotion devices for pushing or pulling sensor array 30 along the pipeline. The type of locomotion device may depend on whether the pipeline is being installed, and/or whether the pipeline is carrying fluid.

For example, carrier 51 may be a pipeline "pig" or similar carrier for in-line inspection tools. Sensor array 30 may be mounted on and propelled with the pig, which is propelled by the flow of fluid in the pipeline. The use of pigs is known in the field of pipeline maintenance. Pig tools have been developed to carry and protect various sensors. The pig is inserted into a launching station, which is typically an oversized section in the pipeline, reducing to the normal diameter. The launching station is then closed and the pressure-driven flow of the product in the pipeline is used to push the pig (and the sensor array 30) along the pipeline until it reaches a receiving station.

For purposes of this description, if carrier 51 is a "pig", that term is meant in a general sense to mean any fluid-propelled carrier that carries sensor array 30 through a segment of the pipeline. In other embodiments, carrier 51 may be a tractor-like device, with wheels or other surface driven propulsion, which can be used to carry sensor array 30 and push or pull the sensor array 30 through the pipeline. Carrier 51 could be self-propelled, such as with an on-board motor, or it could be pulled through the pipeline, such as with a cable.

Typically, carrier 51 will be cylindrical in shape, at least at its front relative to the direction of travel, to carry the ring-shaped sensor array 30. Ideally, the outer diameter of sensor array 30 will be only slightly smaller than the inner diameter of the pipeline.

In some cases, carrier 51 and its sensor payload may be unable to directly communicate with detection unit 52 due to the distance underground or underwater and/or the pipeline material. In this case, carrier 51 may have its own on-board processing and memory to control its movement and record sensor data. The carrier 51 may further have memory to record positional data so that the defect can be located.

In other cases, sensor array 30 may deliver its sensor data to detection unit 52 by various communications links, such as a wireless link. As stated above, a signal is received from each sensor 41 so that localized differences in the interior magnetic field can be detected. Detection unit 51 may also be used to generate and deliver control signals to control the movement of vehicle 51.

Although FIG. 4 illustrates detection unit 52 as being remote from carrier 51 and outside the pipeline, in other embodiments, detection unit 52 may be located on-board carrier 51. In this case, detection unit 52 would have processing and memory devices to record and store data acquired by sensor array 30. This data could be communicated to a remote station (not shown) in real time or subsequently downloaded.

Depending on the complexity of system 500, detection unit 52 could range from a simple output display to a processor-based analysis unit. A skilled operator could interpret a display of the sensor output, or detection unit 52 could have hardware and software to receive and process the sensor data from sensor array 30 and to perform other tasks. Detection unit 51 may store data representing the magnetic fields within the pipeline as they would be expected to appear if the pipeline had no defects. This reference data can then be compared with data received from sensor array 30 to determine the presence of defects along the pipeline. Detection unit 52 can be programmed to analyze the results of the comparison to determine if a coating defect is indicated. The defect's location and size can also be estimated using techniques such as GPS for location and tracking of the carrier's position and speed for defect location and size.

An additional feature of system 500 is its ability to detect the presence of shielding objects or variations in the level of contact between the pipe and surrounding soil. Examples of shielding objects are coating disbondments and low-conductivity rocks and soils. Such objects have an adverse effect on cathodic protection performance. The effect of shielding objects or pipe-to-soil gaps on the magnetic field will result in a degree and shape of asymmetry in the interior magnetic field of the pipeline. This "signature" can be detected and analyzed by detection unit 52 to determine the presence of shielding objects or pipe-to-soil contact variations.

The sensitivity of system 500 could be enhanced by temporarily increasing the current supplied to the pipeline 11 and injecting low frequency ac signals. The low frequency used would depend on the length of pipe needing inspection, but would be kept sufficiently away from 60 Hz and its low order harmonics, in order to be independent of stray currents.

The use of injected ac signals and synchronous detection or narrow bandpass detection at the transmitted frequency, would provide several advantages. The measured magnetic field would not be affected by residual magnetism in the pipe. The measured magnetic field would not be affected by magnetic fields caused by stray currents from electrical power sources. The effect of localized coating breaks, coating disbondments, or pipe-to-soil gaps, or shielding objects would be increased because the capacitive losses of current would be greatly reduced at those locations compared to the normal losses through the coating.

What is claimed is:

1. A method for detecting coating defects in a coated and electrically conductive pipeline, the pipeline being under cathodic protection or otherwise carrying a current applied to its pipe walls, comprising:
   placing a magnetic field sensor array within the pipeline;
   wherein the sensor array comprises a number of magnetic field sensors, arranged in a shape that generally matches but is smaller than the interior profile of the pipeline;
   moving the sensor array along a length of the pipeline;
   receiving output from each sensor of the array;
   comparing the output with the interior magnetic fields of a pipeline without coating defects;
   analyzing the results of the comparing step to determine if a coating defect is indicated, and;
   further analyzing the results of the comparing step to determine the location of the defect both along the length of the pipeline and around the circumference of the pipeline.

2. The method of claim 1, wherein the pipeline is under cathodic protection with a cathodic protection current level, and further comprising applying or increasing the current on the pipeline to a level above the cathodic protection current level.

3. The method of claim 1, wherein the current applied to the pipeline is direct current.

4. The method of claim 1, wherein the current applied to the pipeline is alternating current.

5. The method of claim 1, further comprising analyzing the output to determine if a shielding object or pipe-to-soil gap is present outside the pipeline.

6. The method of claim 1, further tracking the output to determine the size of the coating defect.

7. The method of claim 1, wherein the moving step is performed with a pig type device.

8. The method of claim 1, wherein the moving step is performed with a self-locomotion device.

9. The method of claim 1, wherein the analyzing step is a processor-based step of storing reference data representing the magnetic fields within the pipeline interior in a condition without coating defects, and further comprising using a processor to compare the output data to the reference data.

10. A system for detecting coating defects in a coated and electrically conductive pipeline, the pipeline being under cathodic protection or otherwise carrying a current applied to its pipe walls, comprising:
   a magnetic field sensor array having a number of magnetic field sensors, arranged such that the array has an outer profile that generally matches but is smaller than the interior profile of the pipeline;
   a carrier operable to move the sensor array along a length of the pipeline; and
   a detection unit operable to receive output from each sensor of the array and to store or communicate data representing the output; and
   wherein the detection unit further has processing and memory devices operable to store reference data representing the magnetic fields within the pipeline interior in a condition without coating defects, to compare the output with the reference data, to analyze the results of the comparing step to determine if a coating defect is indicated, and to analyze the output from each sensor to determine the location of the defect both along the length of the pipeline and around the circumference of the pipeline.

11. The system of claim 10, wherein the carrier is a pig type carrier.

12. The system of claim 10, wherein the carrier is a tractor type carrier.

13. The system of claim 10, wherein the carrier is operable to be pulled through the pipeline by means of a cable.

14. The system of claim 10, further comprising a power supply for providing the current applied to the pipeline walls.

15. The system of claim 14, wherein the power supply provides direct current.

16. The system of claim 14, wherein the power supply provides alternating current.

17. The system of claim 10, wherein the processing and memory devices of the detection unit are on board the carrier.

18. The system of claim 10, wherein the processing and memory devices of the detection unit are remote from the carrier.

* * * * *